US008888983B2

(12) United States Patent
Shawcross et al.

(10) Patent No.: US 8,888,983 B2
(45) Date of Patent: Nov. 18, 2014

(54) TREATING A METAL IMPLANT WITH A ROUGH SURFACE PORTION SO AS TO INCORPORATE BIOCIDAL MATERIAL

(75) Inventors: James Timothy Shawcross, Didcot (GB); Andrew Derek Turner, Didcot (GB); David Richard Lewis, Didcot (GB)

(73) Assignee: Accentus Medical Limited (GB)

( * ) Notice: Subject to any disclaimer, the term of this patent is extended or adjusted under 35 U.S.C. 154(b) by 0 days.

(21) Appl. No.: 13/701,119

(22) PCT Filed: May 25, 2011

(86) PCT No.: PCT/GB2011/050984
§ 371 (c)(1),
(2), (4) Date: Nov. 30, 2012

(87) PCT Pub. No.: WO2011/154715
PCT Pub. Date: Dec. 15, 2011

(65) Prior Publication Data
US 2013/0075267 A1   Mar. 28, 2013

(30) Foreign Application Priority Data

Jun. 11, 2010 (GB) .................................. 1009772.3

(51) Int. Cl.
*C25D 5/02* (2006.01)
*A61L 27/04* (2006.01)
(Continued)

(52) U.S. Cl.
CPC ... *C25D 5/02* (2013.01); *A61F 2/30* (2013.01); *A61L 2300/102* (2013.01); *A61L 27/04* (2013.01); *C25D 11/022* (2013.01); *A61L 27/54* (2013.01); *C25D 11/024* (2013.01); *C25D 11/26* (2013.01); *A61L 2400/18* (2013.01)
USPC ........................................................ 205/199

(58) Field of Classification Search
CPC ......... A61F 2/28–2/4684; C25D 11/00–11/34; C25D 5/02–5/022

USPC ........................................................... 205/199
See application file for complete search history.

(56) References Cited

U.S. PATENT DOCUMENTS 5,354,390 A    10/1994  Haszmann et al.
7,713,307 B1 * 5/2010  Hall et al. ................. 623/23.55
(Continued)

FOREIGN PATENT DOCUMENTS

EP          1231299        1/2012
WO          00/72776 A1    12/2000
(Continued)

OTHER PUBLICATIONS

International Search Report for PCT/GB2011/050984 dated Nov. 18, 2013.

(Continued)

*Primary Examiner* — James Lin
*Assistant Examiner* — Ho-Sung Chung
(74) *Attorney, Agent, or Firm* — Tumey L.L.P.

(57) ABSTRACT

Metal implants (10) are treated by anodising the surface (11, 12) in contact with an electrolyte, and then briefly subjecting the anodised surface to a reversed voltage. During a first anodising stage the surfaces are passivated, while during a subsequent anodising stage pits are formed in the passivating surface layer. Rough portions (15) of the surface, in particular portions produced by plasma spraying of metal powder, are sealed with a watertight cover (20) during at least part of the anodising process. After rinsing, biocidal metal ions are subsequently absorbed into the surface of the implant. This provides the implant with biocidal properties. The use of the cover (20) enables a more uniform geometric distribution of biocidal metal ions to be achieved.

12 Claims, 1 Drawing Sheet

Figure 1:
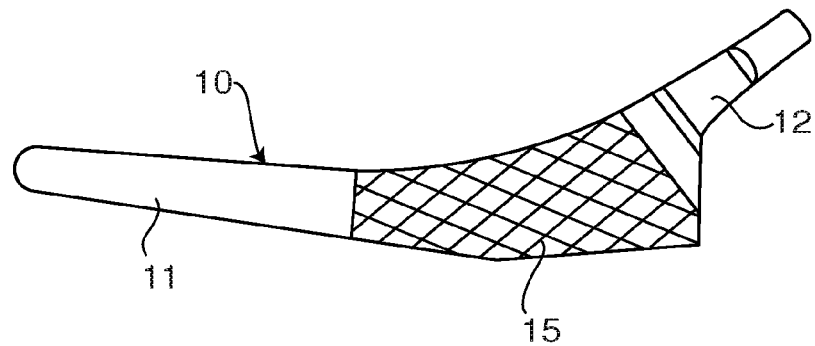

(51) Int. Cl.
*C25D 11/02* (2006.01)
*A61L 27/54* (2006.01)
*C25D 11/26* (2006.01)
*A61F 2/30* (2006.01)

(56) References Cited

U.S. PATENT DOCUMENTS

2006/0229715 A1* 10/2006 Istephanous et al. ........ 623/1.46
2007/0181221 A1* 8/2007 Pickford et al. ............. 148/239
2009/0198344 A1 8/2009 Prentice 2009/0220561 A1* 9/2009 Jin et al. ........................ 424/423

FOREIGN PATENT DOCUMENTS

| WO | 03/089023 A1 | 10/2003 |
| WO | WO 03094774 A1 * | 11/2003 |
| WO | 2006/065205 A1 | 6/2006 |
| WO | WO 2009044203 A1 * | 4/2009 |

OTHER PUBLICATIONS

Written Opinion for PCT/GB2011/050984 dated Nov. 18, 2013.

* cited by examiner

TREATING A METAL IMPLANT WITH A ROUGH SURFACE PORTION SO AS TO INCORPORATE BIOCIDAL MATERIAL

The present invention relates to a method of treatment of a metal object to provide it with biocidal properties. In particular but not exclusively, the invention relates to treated metal objects that provide a reduced risk of infection when the object is implanted by a surgical procedure.

In surgery, metal implants may be inserted into the tissue of the body, either into soft or hard tissue. In the case of cancer treatment of the bone for example, cancerous bone tissue is removed, and a prosthetic metal implant is used to replace that part of the bone that has been removed. Implants are also used for partial or full replacement of bones in joints (e.g. hips) and also in other fields such as dentistry and maxillofacial surgery. Implants for the foregoing (and other) uses may be of titanium metal or titanium alloy. Titanium metal and titanium alloys are biocompatible, relatively strong and relatively light. They may be given a polished shiny surface, or may be given a porous rough surface by plasma spraying with titanium powder, such a porous rough surface potentially providing benefits where bonding of bone onto the implant is desired.

There is a risk of introducing infection, or infection occurring, at the surface of metal implants. A way of treating an implant so that this risk of infection is suppressed is described in WO 2009/044203. This involves anodising the implant at a voltage typically up to 100 V in such a way as to generate a hard oxide layer in which there are pits containing ion-absorbent material, into which silver ions are subsequently absorbed. Although this process provides good results, there are problems in applying it to implants where part of the surface has a porous rough finish, for example produced by plasma spraying of metal powder, vapour deposition or coating with fibrous or sintered metals. One problem is that the anodising current predominantly flows through the area with the porous rough finish, leading to local heat generation; there may also be a detrimental impact on the adherence of the plasma sprayed coating.

The present invention accordingly provides, in a first aspect, a method of treating a metal implant, the implant having a part of its surface provided with a rough metal finish, so as to incorporate a biocidal material in leachable form in the surface, the method comprising:
(a) enclosing the part of the surface with the rough metal finish with a watertight cover;
(b) contacting the metal object with an anodising electrolyte, and applying an anodising voltage to the metal object to passivate the metal by forming an anodised integral surface layer on the metal object;
(c) then removing the watertight cover; and, either before or after step (c),
(d) contacting the anodised metal object with a solution containing a biocidal material so as to incorporate said biocidal material into the surface layer.

The invention is applicable to metal implants formed of metals such as titanium and alloys of titanium, or other valve metals such as niobium, tantalum or zirconium or their alloys, and also to those plated or coated with such metals or their alloys. One standard alloy for this purpose is titanium 90% with 6% aluminium and 4% vanadium (British Standard 7252).

Typically before performing steps (c) and (d) the implant is subjected to the steps of
(e) continuing the application of an anodising voltage to produce pits through the integral surface layer formed in step (b);
(f) then producing a hydrous metal oxide or phosphate in the surface layer by electrochemical or chemical reduction in contact with an electrolyte or a solution; and
(g) then removing or separating the anodised metal object resulting from step
(f) from the electrolyte or the solution of step (f) and rinsing it.

These steps ensure satisfactory ion-absorbing capacity in the anodised surface. The voltage applied during the pit-forming step (e) may be less than the maximum voltage applied during the passivating step (b). The pit formation step may use the same electrolyte as that used during passivation.

During anodisation, step (b), the maximum voltage applied determines the thickness of the passive oxide film. Lower voltages applied subsequently do not affect the film thickness. The maximum voltage may be as high as 2000 V, but is more typically between 30 V and 150 V, for example 100 V. The voltage during passivation, step (b), may be applied as a voltage increasing linearly with time to a maximum, limiting value, or alternatively stepped voltages up to the maximum limit.

The voltage applied during pit formation, step (e), may have a lower value. Surprisingly, this has the effect of increasing both the rate and extent of pit development. Preferably the applied voltage during step (e) is between 15 V and 80 V such as 25, 30, or 75 V. Desirably it is between 20 V and 60 V, for example 25 V or 30 V.

Gentle agitation may be desirable during the passivation step (b) when high currents flow, in order to minimise local heating effects. This is beneficial in improving process uniformity over a single item, and also over a group of units being treated simultaneously. Preferably, movement or circulation of the electrolyte relative to the surface of the metal implant is suppressed or inhibited during step (e) when microscopic pits are being formed.

The electrolyte may be acid or alkaline. For example it may be phosphoric acid at a concentration between 0.01 M and 5.0 M, typically from 0.1 M to 3.0 M and in particular 2.0 M, in a solvent such as water. Other electrolytes such as sulphuric acid, phosphate salt solutions or acetic acid may be used. Preferably, the pH of the acidic electrolyte should be maintained within the range of $0.5<pH<2.0$—more ideally within the range $0.75<pH<1.75$. If an alkaline electrolyte is used the pH is preferably greater than 9 and more typically the pH is in the range of 10-14. The alkaline electrolyte can be a phosphate salt such as $Na_3PO_4$, or may be sodium hydroxide, NaOH.

The geometric surface area of the metal implant can be determined by conventional means. This does not however take into account microscopic surface features or surface roughness of the metal, and the microscopic surface area is an important factor in determining and controlling how much current is passed during the anodisation step. The microscopic surface area can be determined, for example, by immersion of the metal and implant in an electrolyte, and measuring the double layer capacitance and comparing this to calibrated standards. The ratio of microscopic to geometric area is known as the surface roughness factor. A polished surface typically has a surface roughness factor less than 2; in contrast a surface roughened by the provision of plasma sprayed titanium may have a surface roughness factor as much as 100, and therefore that part of the surface would draw a much larger electrical current. The term "rough metal finish" means that the surface roughness factor of that portion of the surface is at least 5, typically at least 20 or 40, and may be as high as 200 or up to 500 or more.

The watertight cover is designed to prevent contact with solutions used in the method of treating the metal implant, such as the anodising electrolyte. By protecting the part of the surface that has the rough metal finish from the electrolyte during the anodising steps, the problems that would be caused by the very large currents are avoided. The watertight cover may comprise a material that is spread over the rough surface, such as a paint, grease or wax, or heat- or UV-cured resin, and that can subsequently be easily removed for example by heat treatment. Alternatively it may be in the form of a sheet, tape or sleeve of impermeable material, such as polyimide, silicone or polyethylene, which is sealed along its edges onto the surface of the metal implant. In another example the watertight cover may be provided by one or more rigid bodies arranged to enclose the rough part of the surface, and sealed around their edges onto the surface of the metal implant.

In a modified procedure, the entire implant is initially subjected to anodising up to a voltage less than 40 V, more preferably less than 35 V such as 28 V. This may be performed in conjunction with cooling of the electrolyte to less than 10° C., more preferably less than 5° C., and still more preferably less than 2° C. The implant is then subjected to the procedure described above, anodising those portions that are not protected by the cover to a higher voltage such as 100 V.

In a further modification the initial lower-voltage anodising is at a voltage less than 5 V, for example between 0.5 and 2.5 V, either to the surface of the entire implant or to only the rough part. Although this generates an oxide layer which is very thin (at 1 volt the thickness is only 1.4 nm), it ensures that the oxide is of substantially uniform thickness. Alternatively such a thin oxide layer may be formed by a chemical process, using a chemical oxidising agent. For example this might involve emotion in nitric acid. In any event, after forming such a thin oxide layer, the implant is then subjected to the procedure described above, anodising those portions that are not protected by the cover to a higher voltage such as 100 V.

Whether or not the rough part of the surface has been subjected to any anodising, it has been found that a rough surface formed by plasma spraying of titanium powder has some ion exchange capacity, sufficient to absorb biocidal material such as silver ions. So if the cover is removed, and then the entire implant immersed in an aqueous solution of silver ions, then silver ions are absorbed over the entire surface. After implanting the implant in a surgical procedure, such ions gradually leach out from the anodised surfaces and from the plasma sprayed titanium surface, and suppress any infection.

The reduction step, step (f), as a first option, comprises applying a negative voltage to the metal object that has been anodised during steps (b) and (e), while the metal object remains in contact with the anodising electrolyte; this preferably uses a low voltage insufficient to cause electrolysis of the solvent. For example, in the case of a medical implant comprising titanium, if the electrolyte is 2.1 M phosphoric acid, the negative voltage may be in a range of from −0.2 to −0.7 V with respect to an Ag/AgCl standard reference electrode. This voltage range avoids electrolysis of the water solvent, which will occur at voltages below −0.7 V.

As a second option, the metal object that has been anodised during steps (b) and (e) may be put into contact with an electrolyte solution containing a reducible soluble salt of titanium or of the substrate metal, and subjected to a negative voltage to bring about electrochemical reduction. As a third option for step (f), instead of performing electrochemical reduction, the metal object may be contacted with a chemical reducing agent.

After anodisation in steps (b) and (e), it is believed that the solution contained within the surface pits contains a peroxy cationic complex of the substrate metal. This complex can be reduced electrochemically to a hydrous metal oxide of limited solubility, as in the first option for step (f) described above. This complex can similarly be reduced chemically, as in the third option for step (f). Rather than relying on this complex remaining in the pits, in the second option for step (f) an electrolyte solution is provided that contains a peroxy cationic complex, preferably a peroxytitanyl, which can be reduced electrochemically within the pits to hydrous titania.

Instead of using an external source of electricity for electrochemical reduction, the metal object may be made negative by connecting it electrically to an electrode of a corrodible metal, such as iron or steel; this may be immersed in the same electrolyte as the metal object, or in a separate electrolyte with ionic connection through a salt bridge or an ion-selective membrane. The corrodible metal electrode corrodes preferentially, so causing electrochemical reduction at the surface of the metal object.

Preferably, in step (g), the metal object is rinsed to remove any electrolyte or solution remaining on the surface after the preceding steps. The rinsing may use water or any appropriate solvent. Then, in step (d), there is contact with the solution containing the biocidal material, which is preferably in the form of metal ions, to incorporate biocidal material into the surface layer on the metal object.

The biocidal material may comprise a biocidal metal such as silver, although other metals may be used in addition to or as alternatives to silver, for example copper, ruthenium or platinum. Preferably, the biocidal material (e.g. metal, such as silver) is provided in the solution of step (d) in the form of ions. A suitable surface concentration of silver, on a geometric basis, is in the range 2 to 30 $\mu g/cm^2$, more typically in the range 2 to 15 $\mu g/cm^2$, preferably 4 to 6 $\mu g/cm^2$; such concentrations are efficacious in suppressing infection, but are not toxic. In some situations it will be appreciated that still higher silver loadings may be desirable, that are efficacious in suppressing infection, but are not toxic.

The present invention provides, in a second aspect, a method of treating a metal implant, the implant having a part of its surface provided with a rough metal finish, so as to incorporate a biocidal material in leachable form in the surface, the method comprising:

(a1) selecting an anodising electrolyte that provides a low anodising current density;

(b1) contacting the metal object with the anodising electrolyte, and applying an anodising voltage to the metal object to passivate the metal by forming an anodised integral surface layer on the metal object, the anodising voltage being increased at a slow controlled rate not exceeding 0.5 V/s; and then (d) contacting the anodised metal object with a solution containing a biocidal material so as to incorporate said biocidal material into the surface layer.

The low anodising current density may be provided by an electrolyte which is at a low temperature, i.e. <10° C., more preferably <5° C., for example at 1° C. for 2.1 M phosphoric acid; or has a low concentration, i.e. <1 M, more preferably less than 0.4 M, for example 0.1 M phosphoric acid at 20° C.; or is both at low temperature and of a low concentration. The use of lower temperature electrolyte reduces the diffusion coefficients, and reduces the solubility of Ti(IV) in the electrolyte, and so reducing inefficient side processes. A low anodising current density is also enhanced by using an electrolyte whose pH is less extreme, i.e. for an acid solution the pH should be higher than normal e.g. pH 0.85 for 2.1 M phosphoric acid, and for an alkaline solution the pH should be lower than normal, as this moderates the solubility of Ti(IV). Furthermore the voltage should be raised gradually, for example between 0.01 and 1 V/s, preferably less than 0.5 V/s, for example at only 0.2 V/s. This is beneficial at least partly in ensuring time for the surface to be close to an equilibrium state; use of a slow rate of voltage increase also gives a lower current density, because the oxide layer grows at a slow rate. (In comparison anodising would more usually be carried out with 2.1 M phosphoric acid at 20° C., raising the voltage at between 0.5 to 5 V/s.)

This second aspect of the invention enables the entire surface including the porous metal coating to be anodised, either to passivate or to produce surface pits, as described previously. Performing the anodising in this way reduces the localised power consumption at the surface of the implant. Nevertheless it may not be entirely satisfactory, as the provision of an ion-absorbing anodised surface over a rough surface with a roughness factor of 100 may provide an excessively high silver concentration, considered on a geometrical basis. For example a monolayer of silver adsorption onto an anodised surface would give a microscopic concentration of about 0.3-1.0 µg/cm$^2$, which would correspond to a geometric loading of 30-100 µg/cm$^2$. Hence an implant that has been anodically passivated, but where pit formation has not been performed, may be excessively loaded in silver in the rough part of the implant while potentially providing too low a loading in the polished part of the surface.

As an option, in this second aspect of the invention, before performing step (d) the implant is subjected to the steps of
(e) continuing the application of an anodising voltage to produce pits through the integral surface layer formed in step (b1);
(f) then producing a hydrous metal oxide or phosphate in the surface layer by electrochemical or chemical reduction in contact with an electrolyte or a solution; and
(g) then removing or separating the anodised metal object resulting from step
(f) from the electrolyte or the solution of step (f) and rinsing it.

Although this would ensure a satisfactory loading in the polished part of the surface, it may be too high a loading in the rough part of the implant for some applications.

Where it is desirable to achieve substantially uniform biocidal material concentration, on a geometrical basis, it is therefore preferable to treat the polished surfaces and the rough surfaces separately, as can be achieved using the cover specified in the first aspect of the invention.

The present invention also provides metal implants produced by such methods.

Implants according to the invention can be used for many medical and surgical purposes, including full and partial hip replacements, implants useful in maxillofacial, trauma, orthodontal and orthopaedic applications, dental implants, and any other applications where a metal implant is provided in part with a porous rough surface.

Figure 2:
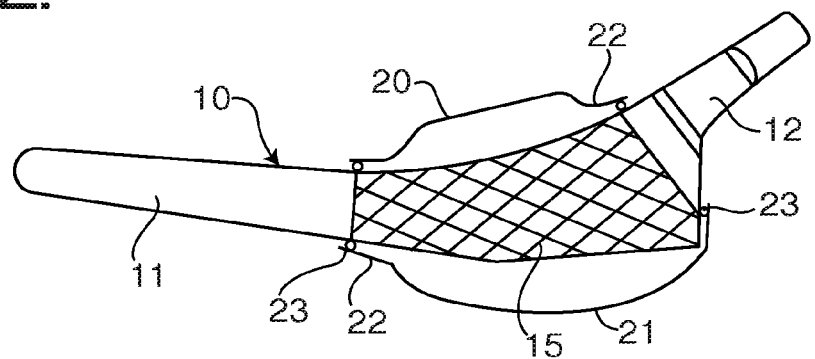
Figure 3:
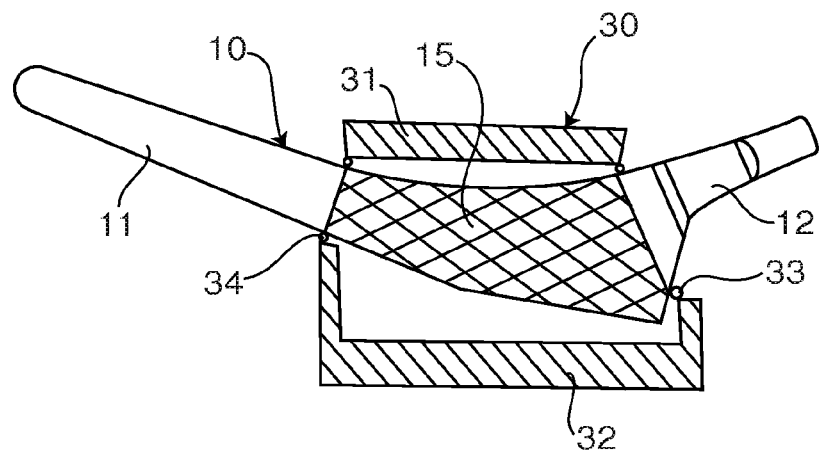

The invention will now be further and more particularly described, by way of example only, with reference to the accompanying figures, in which:

FIG. 1 shows a side view of a hip replacement implant;
FIG. 2 shows a view of the implant of FIG. 1 provided with a protective sleeve shown in section; and
FIG. 3 shows a view of the implant of FIG. 1 held by a protective clamp shown in section.

Referring to FIG. 1 there is shown a hip joint implant 10 of titanium alloy, with two end portions 11 and 12 that are polished, and a central portion 15 provided with a porous metal coating such as plasma-sprayed titanium powder coating (represented by cross hatching) of thickness about 0.5 mm. The roughness factor of the polished surface is about 1.5, whereas (from capacitative measurements) the roughness factor of the plasma-sprayed portion 15 may be about 100.

In experimental specimens, with a plasma-sprayed titanium coating of thickness 0.1 mm, the roughness factor of the plasma-sprayed surface was about 27; with a coating of thickness 0.2 mm the roughness factor was 86; while with a plasma-sprayed titanium coating of thickness 0.5 mm the roughness factor was 147. The roughness factor observed in relation to the hip joint implant 10 of FIG. 1 is in conformity with these experimental figures.

By anodising the surface of an implant 10 the surface may be given enhanced ion-exchange properties. It will be recognised that, for example, the tapered end of the end portion 12 may not be treated, to allow electrical connection to be made to the implant 10.

By way of experiment titanium rods that had been plasma spray coated on one half were anodised at a low scan rate of 0.15 V/s up to a maximum voltage of 30 V, using as electrolyte 2.1 M phosphoric acid, in a first case at 0° C. and in a second case at minus 15° C. In the first case this was performed for 1.34 h (so that pit formation occurred), while in the second case anodising was stopped after 0.17 h (10 min), so that only passivation occurred. After rinsing, the rods were then immersed in 0.1 M silver nitrate solution for 1 hour. In the first case the resultant geometric loading of silver was 170 µg/cm$^2$ averaged over the entire surface; and even in the second case, where minimal pit formation had occurred, the resultant geometric loading of silver on the rough portion was 45 µg/cm$^2$. These loadings may be excessive for some applications, particularly in the rough areas.

As a further experiment, plasma-sprayed titanium surfaces were immersed in silver nitrate solution for 2 h without any anodising. The resultant silver loadings were variable, and depended to some extent on the concentration of the silver nitrate solution (which was varied between 0.01 and 0.10 M); but in each case the loading was between 4 and 14 µg/cm$^2$, which is an acceptable geometrical loading.

Hence satisfactory biocidal properties can be given to an implant as shown in FIG. 1 by masking the plasma-sprayed rough portion 15 with a watertight cover. As indicated in FIG. 2, a watertight cover 20 may comprise a loose-fitting plastic sleeve 21 with heat-shrinkable end sections 22, which are then sealed onto the polished portion of the implant 10 by a narrow bead or thread of resin 23 cured by ultraviolet radiation, the bead or thread being of width of 0.5 mm. After attaching this watertight cover 20, the implant 10 can be immersed in electrolyte and anodised.

As an alternative, the rough portion 15 may be entirely coated with a resin which is then cured by heat or UV in situ, the coating preferably extending just onto the polished portion for example to a distance of 0.5 mm. The resin may be coated directly onto the metal, or alternatively the rough portion 15 may be first covered with a tape or film, which is then covered with the coating of resin, and the resin is then cured in situ; this reduces the difficulty of subsequently removing the cured resin.

After masking the rough portion 15 with the watertight cover 20, the implant 10 in this example is anodised using a maximum voltage of 100 V, to produce a hard wearing anodised oxide surface layer. In this example the electrolyte is 2.1 M phosphoric acid at about 20° C., and the voltage may be increased gradually at for example 1 V/s up to the maximum value. Alternatively the target or maximum voltage may be reached by limiting the current density so it does not exceed for example 5 mA/cm$^2$. The anodising current results in formation of an oxide layer that is integral with the titanium metal substrate, passivating the surface. The current falls to a low level once the maximum voltage has been achieved, for example less than 1 mA/cm$^2$ and this drop in current indicates that passivation has been completed. The anodising voltage is then maintained to form pits in the surface, the pits typically having depths in the range 1 to 3 µm penetrating through the outer passive hard oxide layer (which is 0.14 µm thick at 100 V) into the substrate, and have typical diameters of 1 to 5 µm. The pits may occupy some 5 to 20% of the surface area, though preferably below 10%, so they do not significantly affect the hard wearing properties of the hard surface layer. If the anodising voltage is maintained at the maximum value, 100 V, the pit formation typically takes a further 2 or 3 hours, whereas if the voltage is reduced to 25 V after passivation, for example, the pit formation is more rapid, and may be completed in less than 0.5 h. Once the passivation and the production of pits to a required format are complete, the implant 10 is subjected to a brief voltage reversal which results in an observed negative current. With the aqueous 2.1 M phosphoric acid solution as electrolyte, the reversed voltage is between −0.2 and −0.7 V, for example about −0.45 V (as measured with respect to a Ag/AgCl standard reference electrode), to ensure that the solvent, water, is not electrolysed, but that a reduction process is able to take place. During this period of reversed voltage, certain titanium species are electrochemically reduced within the pits to high surface area, low solubility, hydrous titanium oxide species, and so the pits fill with this high surface area inorganic medium, and the current through the implant drops and eventually falls to zero or substantially zero. The reversed voltage step may take from 60 to 180 s.

The surface of the anodised implant 10 is rinsed with de-ionised water to remove phosphoric acid residues and other soluble materials. The sleeve 20 is then removed to expose the plasma-sprayed rough portion 15. The implant 10 is next immersed in a solution comprising the biocidal material, which is silver in this example, typically for between 0.5 hours and 2 hours, for example 1 hour. The solution is an aqueous solution of silver nitrate having a silver concentration in the range of from 0.001 to 10 M, e.g. 0.01 to 1.0 M, for example, 0.1 M or thereabouts. In a specific example the implant 10 would be immersed in 0.1 M silver nitrate solution for 1 hour. Silver ions are absorbed within the surface, primarily by ion exchange, the greatest concentration being in the material within the pits. The implant 10 is then removed from the silver solution, rinsed and can be dried, packaged and sterilised for subsequent use. In this case the concentration of silver ions, on a geometrical basis, can be expected to be between 4 and 14 µg/cm$^2$ over the entire surface of the implant.

In a modification, after rinsing the surface of the anodised implant 10, but without removing the sleeve 20, the implant 10 might be immersed in 0.1 M silver nitrate solution for 1 hour. The sleeve 20 may then be removed, and the implant 10 then immersed in a lower concentration of silver nitrate, such as 0.02 M. This will not significantly affect the concentration of silver in the anodised portions 11 and 12, but leads to a slightly lower concentration of silver in the plasma sprayed rough portion 15. Alternatively the rough portion of the implant 15 could be immersed in the silver nitrate solution for a shorter period of time or in a lower pH solution to prevent excessive silver loading. This approach is also applicable if the rough portion of the implant 15 has been anodised. And in a further alternative, after rinsing the surface of the anodised implant 10, the sleeve 20 is removed and the implant 10 immersed in silver nitrate solution of lower concentration, such as 0.02 M; the end portions 11 and 12 are then immersed in higher concentration silver nitrate, such as 0.1 M, for a period such as 1 hour. The end portions 11 and 12 may be immersed successively, or alternatively the rough portion 15 may be covered again, and the end portions 11 and 12 immersed simultaneously.

In an alternative modification, the entire surface of the implant 10 is subjected to at least some anodising treatment. In one example, after performing the anodising (passivation, pit formation and voltage reversal) as described above, the sleeve 20 is removed, and the implant 10 is then subjected to a second anodising process to a peak voltage between 25 and 30 V for only 10 minutes (corresponding to passivation only). This ensures that the rough portion 15 is passivated. The implant 10 can then, after rinsing, be immersed in a silver nitrate solution as described above. For example it might be immersed in a low concentration solution, such as 0.005 M for a brief period such as 0.25 h, to reduce the adsorption of silver. The polished end portions 11 and 12, if desired, can then be subsequently immersed in a higher concentration solution of silver nitrate, such as 0.1 M, to ensure adequate silver loading in those end portions 11 and 12.

In another modification the implant 10 (FIG. 2) is subjected to anodising, but in this case with the sleeve 20 in position the end portions 11 and 12 are anodised to only 30 V maximum voltage for about half an hour (e.g. for a time between 20 minutes and 40 minutes), corresponding to passivation and pit formation, followed by voltage reversal. The sleeve 20 is then removed to expose the rough portion 15, and the entire implant is then anodised for a short period of time such as 0.1 h (about 5 minutes). The anodised implant 10 would then be rinsed, and immersed in silver nitrate solution as described above.

In another modification the implant 10 is subject to anodising in 2.1 M phosphoric acid but in this case the entire surface including the rough portion 15 is anodised to a maximum of 28 V by increasing the voltage at 0.5 V/s to passivate the surface. The implant is then removed from the electrolyte and rinsed, and a watertight cover such as the sleeve 20, or a UV-cured masking resin, is applied to the implant 10 to cover the rough portion 15. The end portions 11 and 12 of the implant 10 are then anodised to 100 V increasing the voltage at 1 V/s. The voltage is maintained at 100 V until pit formation has occurred (e.g. 1-3 hrs) and is then followed by a voltage reversal as described above. The implant is then removed from the electrolyte, rinsed, and the watertight cover removed before immersion in silver nitrate solution as described above.

It will be appreciated that some of these alternatives will be determined by the desired appearance of the final product, as anodising to a maximum voltage of about 30 V provides the surface with a blue appearance, whereas anodising to a maximum voltage of about 100 V provides the surface with a mauve appearance. A similar mauve/purple appearance can also be achieved at 25-28 V. Hence in the previously-described process, in which the rough portion 15 is anodised to 28 V whereas the end portions 11 and 12 are anodised to 100 V, the colours are substantially the same. Alternative electrolyte compositions may also be used to influence the colour and appearance of the implant.

The various procedures described above all made use of a sleeve 20 to cover the rough portion 15 of the implant 10, or a coating of resin cured in situ. It will be appreciated that alternative means may be used to cover the rough portion 15 and to seal it from the electrolyte. Referring now to FIG. 3, the implant 10 is shown held by a clamp 30 consisting of an upper jaw 31 and a lower jaw 32 that are shaped to match the shape of the rough portion 15, and are sealed to the polished portion of the implant 10 by narrow beads or threads of resin 33 and 34 cured by ultraviolet radiation, the bead or thread being of width of 0.5 mm.

In a modification the clamp 30 has resilient seals 33 and 34 that are permanently fixed to the jaws 31 and 32, sealing by virtue of their resilience rather than being bonded to the implant 10. This simplifies the fitting and re-use of the enclosing clamp 30.

In use of the treated implant 10 it is thought that during exposure to body fluids there is a slow leaching of silver species from the surface, whether from the anodised layer or from the rough portion 15, so that the growth of microorganisms such as bacteria, yeasts or fungi in the vicinity of the metal object is inhibited. The leaching is thought to be effected by ion exchange of silver on the metal object with sodium in the body fluids that contact the metal object. Other mechanisms can occur, such as the oxidation to ionic species of any photo-reduced silver retained in the hydrous metal oxide as a result of the localised oxygen levels, to produce the released silver ions which can go on to kill or suppress the growth of the microorganisms or biofilm formation.

It is to be understood that references herein to silver as a biocidal metal also apply to other biocidal metals, such as copper, gold, platinum, palladium or mixtures thereof, either alone or in combination with other biocidal metal(s).

It is to be understood that additional coatings of for example those to enhance osseointegration such as tri-calcium phosphate or hydroxyapatite may be provided on the porous rough metal surface of portion 15 following any of the treatment methods above.

Although individual embodiments of the invention are discussed, it is to be understood that combinations of the individual embodiments fall within the scope of the invention as claimed and described. It will also be appreciated that the processes are applicable to implants of any shape and size. The invention is applicable where the rough portion extends to one end of an implant. However the invention is particularly advantageous where the rough portion is at an intermediate position along the implant, as the invention considerably simplifies the processes required to anodise a single implant, or indeed to anodise several implants simultaneously.

What is claimed:

1. A method of treating a metal implant, the implant having a first part of its surface provided with a rough metal finish having a surface roughness factor of at least 5 and having a second part of its surface provided with a polished surface having a surface roughness factor of less than 2, so as to incorporate a biocidal material in leachable form in the surface, the method comprising:
   (a) subjecting at least the first part of the surface to an anodising step with an anodising electrolyte, by applying an anodising voltage at a first voltage having a maximum value between 25 and 30 V so as to achieve passivation, and then ceasing the anodising process at the first voltage;
   (b) enclosing the first part of the surface with a watertight cover;
   (c) then contacting the metal object with an anodising electrolyte, and performing an anodising step by applying an anodising voltage at a second voltage having a maximum value between 30 V and 150 V to the metal object for sufficient time to passivate the second part of the surface by forming an anodised integral surface layer on the metal object;
   (d) continuing the application of the anodising voltage at the second voltage to produce pits through the integral surface layer formed in step (c);
   (e) then producing a hydrous metal oxide or phosphate in the surface layer by electrochemical or chemical reduction in contact with an electrolyte or a solution; and
   (f) then removing or separating the anodised metal object resulting from step (e) from the electrolyte or the solution of step (e);
   (g) then removing the watertight cover; wherein step (a) is carried out either before applying the watertight cover (step (b)) or after removing the watertight cover (step (g)); and
   (h) then contacting the anodised metal object with a biocidal material solution containing a biocidal material so as to incorporate said biocidal material into the passivated surface of the first part of the surface and the integral surface layer of the second part of the surface by ion exchange.

2. A method as claimed in claim 1 wherein the metal implant is formed of titanium or an alloy of titanium, or niobium, tantalum or zirconium or their alloys, or is plated or coated with such metals or their alloys.

3. A method as claimed in claim 1 wherein the voltage applied during the pit-forming step (d) is less than the maximum voltage applied during the passivating step (c).

4. A method as claimed in claim 1 wherein the watertight cover comprises a material that is spread over the rough surface and can subsequently be easily removed.

5. A method as claimed in claim 1 wherein the watertight cover comprises a sheet or sleeve of impermeable material which is sealed along its edges onto the surface of the metal implant.

6. A method as claimed in claim 1 wherein the watertight cover is provided by one or more rigid bodies arranged to enclose the rough part of the surface, and sealed around their edges onto the surface of the metal implant.

7. A method as claimed in claim 1 wherein during anodising of the implant without the watertight cover the electrolyte is cooled to less than 10° C.

8. A method as claimed in claim 1 wherein during anodising of the implant without the watertight cover the voltage is increased at a slow controlled rate not exceeding 0.5 V/s.

9. A method as claimed in claim 1 wherein the maximum voltage during the anodising step (a) at the first voltage, and the maximum voltage during the anodising step (c) at the second voltage, are selected so as to achieve substantially the same colour of both the first part and the second part of the surface.

10. A method as claimed in claim 9 wherein the maximum voltage during the anodising step (a) at the first voltage is between 25 and 28 V, while the maximum voltage during the anodising step (c) at the second voltage is 100 V.

11. A method as claimed in claim 1 wherein before removing the watertight cover (step (g)), the method also comprises:
   (i) contacting the anodised metal object with a preliminary treatment solution containing a biocidal material so as to incorporate said biocidal material into the integral surface layer of the second part of the surface, wherein the concentration of biocidal material in the preliminary treatment solution is greater than that in the biocidal material solution of step (h).

12. A method as claimed in claim 1 wherein the first part of the surface is a plasma-sprayed surface with a surface roughness factor at least 20.

* * * * *